(12) United States Patent
Burk

(10) Patent No.: US 7,594,509 B2
(45) Date of Patent: Sep. 29, 2009

(54) HEAT AND MOISTURE EXCHANGE DEVICE FOR RESPIRATORY THERAPY

(75) Inventor: Marc Alan Burk, Murrieta, CA (US)

(73) Assignee: Teleflex Medical Incorporated, Durham, NC (US)

( * ) Notice: Subject to any disclaimer, the term of this patent is extended or adjusted under 35 U.S.C. 154(b) by 711 days.

(21) Appl. No.: 11/038,347

(22) Filed: Jan. 18, 2005

(65) Prior Publication Data
US 2006/0157056 A1 Jul. 20, 2006

(51) Int. Cl.
A62B 18/08 (2006.01)
A62B 9/02 (2006.01)
F28F 27/02 (2006.01)

(52) U.S. Cl. ............................ 128/205.24; 128/201.13; 165/103

(58) Field of Classification Search ............ 128/201.13, 128/204.17, 205.24, 207.16, 200.24, 201.25, 128/203.26, 205.29; 251/207, 208, 340, 251/345, 352; 165/103
See application file for complete search history.

(56) References Cited

U.S. PATENT DOCUMENTS

| | | | |
|---|---|---|---|
| 3,575,206 A | 4/1971 | Ulmann | |
| 3,747,598 A | 7/1973 | Cowans | |
| 4,063,913 A | 12/1977 | Kippel et al. | |
| 4,090,513 A * | 5/1978 | Togawa | 128/201.13 |
| 4,133,656 A | 1/1979 | Kippel et al. | |
| 4,168,706 A | 9/1979 | Fletcher et al. | |
| 4,171,962 A | 10/1979 | Kippel et al. | |
| 4,172,709 A | 10/1979 | Kippel et al. | |
| 4,200,094 A | 4/1980 | Gedeon et al. | |
| 4,360,040 A * | 11/1982 | Cove et al. | 137/625.3 |
| 4,431,028 A * | 2/1984 | Hendrick | 137/625.3 |
| 4,548,626 A | 10/1985 | Ackley et al. | |
| 4,598,704 A | 7/1986 | Bordoni et al. | |
| 4,793,342 A | 12/1988 | Haber et al. | |
| 5,033,507 A | 7/1991 | Pouchot | |
| 5,035,236 A | 7/1991 | Kanegaonkar | |
| 5,195,527 A | 3/1993 | Hicks | |
| 5,230,727 A | 7/1993 | Pound et al. | |
| 5,308,040 A * | 5/1994 | Torres | 251/208 |
| 5,331,957 A | 7/1994 | Liu | |
| 5,460,172 A | 10/1995 | Eckerbom et al. | |
| 5,505,768 A | 4/1996 | Altadonna | |
| 5,546,930 A | 8/1996 | Wikefeldt | |
| 5,590,644 A * | 1/1997 | Rosenkoetter | 128/201.13 |
| 5,647,345 A | 7/1997 | Saul | |
| 6,415,788 B1 | 7/2002 | Clawson et al. | |
| 6,550,476 B1 | 4/2003 | Ryder | |
| 6,588,421 B1 | 7/2003 | Diehl et al. | |
| 6,792,946 B1 | 9/2004 | Waldo et al. | |
| 6,976,488 B2 * | 12/2005 | Halperin | 128/201.13 |
| 2002/0017302 A1 * | 2/2002 | Fukunaga et al. | 128/207.14 |

(Continued)

FOREIGN PATENT DOCUMENTS

CH 0671703 A 9/1989

(Continued)

Primary Examiner—Justine R Yu
Assistant Examiner—Arundipta Shome
(74) Attorney, Agent, or Firm—Baker & Hostetler LLP

(57) ABSTRACT

A heat and moisture exchange device for being selectively operated between HME mode and bypass mode comprises a rotatable valve and valve selector configured to be rotated without transferring rotational movement to tubing attached to the device.

13 Claims, 5 Drawing Sheets

U.S. PATENT DOCUMENTS

| | | |
|---|---|---|
| 2004/0084046 A1 | 5/2004 | Halperin |
| 2004/0118402 A1 | 6/2004 | Heinonen |
| 2004/0123974 A1 | 7/2004 | Marler et al. |

FOREIGN PATENT DOCUMENTS

| | | |
|---|---|---|
| JP | 408252315 | 10/1996 |
| WO | WO 99 60954 A1 | 12/1999 |
| WO | WO 2005/047797 A2 | 5/2005 |

* cited by examiner

HEAT AND MOISTURE EXCHANGE DEVICE FOR RESPIRATORY THERAPY

BACKGROUND OF THE INVENTION

Heat and moisture exchange devices are often used to provide moisture to gases from a ventilator for respiratory therapy. To this end, a heat-moisture exchanger (HME) is positioned in the respiratory circuit, such a device containing a material or composition capable of absorbing heat/moisture from patient exhaled gas and desorbing the heat/moisture into the cool/dry respiratory gas stream from the ventilator for patient inhalation.

For treating some respiratory conditions, it is desirable to introduce an aerosol generated by a nebulizer to the gas delivered to a patient. When such treatment is provided, it is desirable to bypass the HME to avoid absorption of the aerosol in the HME material. To avoid the inconvenience and inefficiency of removing the HME device each time aerosol treatment is to be administered, HME bypass devices have been designed, such as described in U.S. Patent Application Publication No. 2004/0084046. However, operating the prior art device between HME and bypass functions requires rotation of the housing portions causing rotation of the pipes at each end of the housing portions. Such housing and pipe rotation is transferred to the attached patient circuit tubing resulting in disturbing or loosening the pipe connections and contributes to inadvertent tubing disconnects affecting patient ventilation or necessitates repositioning of the patient ventilator circuit to relieve the added torque along the tubing.

SUMMARY OF THE INVENTION

The heat and moisture exchange device described herein is provided with a mechanism that allows an operator to select and change the mode of operation between HME and aerosol treatment, but does not transfer rotation and torque to the patient respiratory circuit tubing. The device comprises a housing wall structure defining an interior chamber in which is positioned a heat and moisture exchange (HME) material or composition capable of absorbing moisture and heat from a patient exhaled gas and thereafter releasing the absorbed heat and moisture into a dry respiratory gas for patient inhalation. Within the walled housing are a heat and moisture exchange passageway and a bypass passageway. Stationary pipes secured on opposite ends of the housing communicate with the interior chamber. A valve adjacent to the distal pipe end is configured to provide selective fluid communication through the HME passageway or the bypass passageway, the valve including a valve selector providing such selective communication without moving the wall structure or either of the end pipes relative to one another. The selectively operated valve comprises a first apertured wall and a second apertured wall. One wall is stationary, and the other is moved by the valve selector to align apertures for selectively directing fluid flow through the HME passageway or the bypass passageway. In a preferred embodiment, the valve selector is rotatably mounted on the device housing whereby an operator can conveniently rotate the valve selector, causing rotation of the movable apertured member for selectively aligning apertures to direct fluid flow for HME or bypass operation.

DETAILED DESCRIPTION OF THE PREFERRED EMBODIMENT

Figure 1:
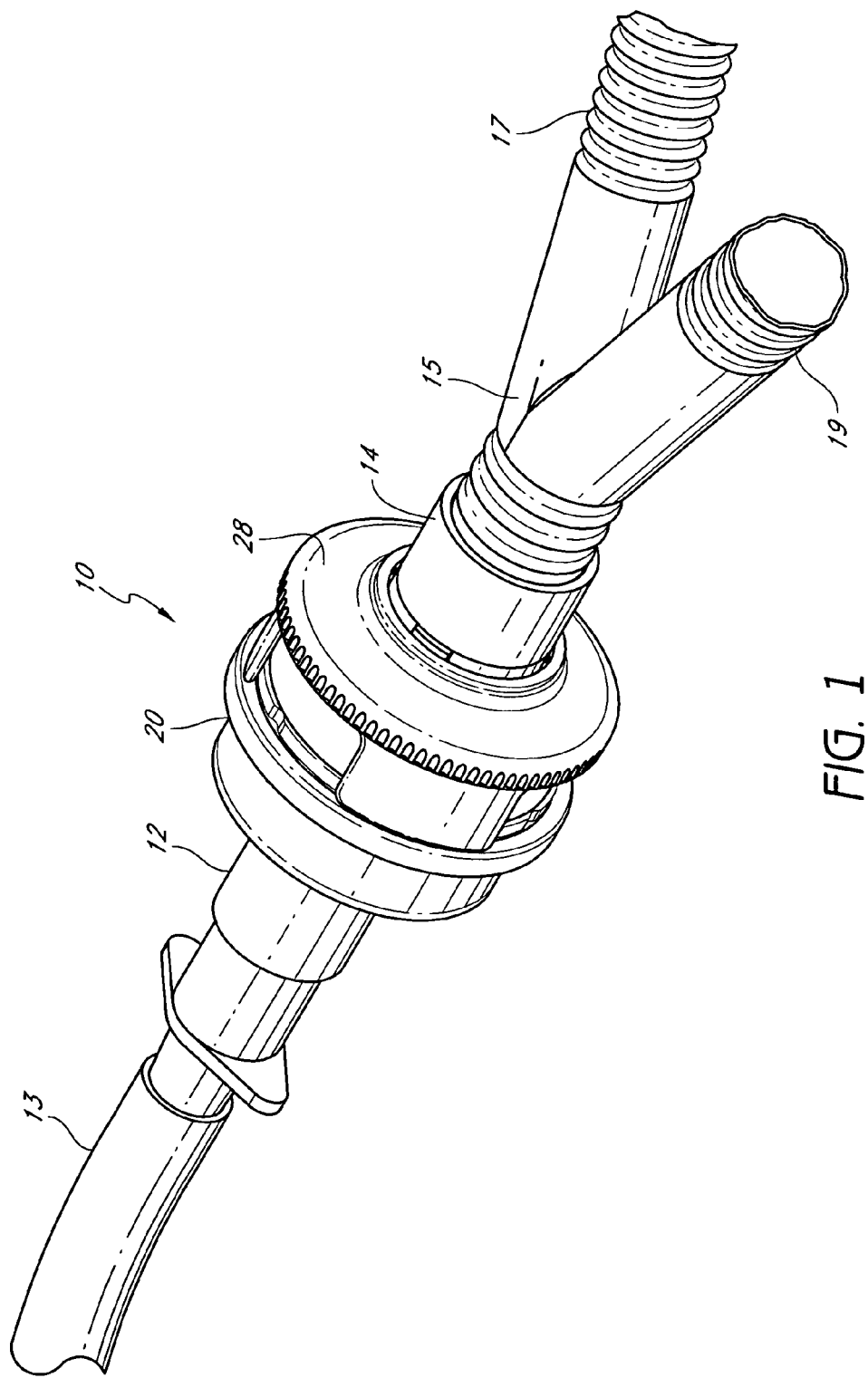
FIG. 1 is a perspective view of the heat and moisture exchange device with ventilator circuit tubing attached at one end and a patient gas delivery tube attached at the opposite end.

FIG. 1 shows an exterior view of the heat and moisture exchange device (HME) 10 with housing wall 20 having pipes 12 and 14 secured on the housing at opposite ends. Proximal end pipe 12 is secured to a tracheal tube 13 or to an endotracheal tube or other patient airway interface. At the opposite end of the housing is distal end pipe 14 to which is secured a ventilator circuit wye 15 and tubing assembly including inspiratory and expiratory circuit tubes 17 and 19. Such respiratory or ventilator circuit tubing and assemblies and patient gas delivery tubing, such as tracheal tube or endotracheal tubes or other patient gas delivery tubes, are not a part of the heat and moisture exchange device, are well understood by those skilled in the art and will not be described in further detail. Also shown is a valve selector 28 rotatably mounted relatively to the housing adjacent to pipe 14. Other tubing configurations may be secured to respective ends of the HME device. The tubing assembly includes a nebulizer or metered dose inhaler (not shown) for generating a medicated aerosol to be delivered to the patient through the HME device in a bypass mode, as will be described further hereinafter.

Figure 2:
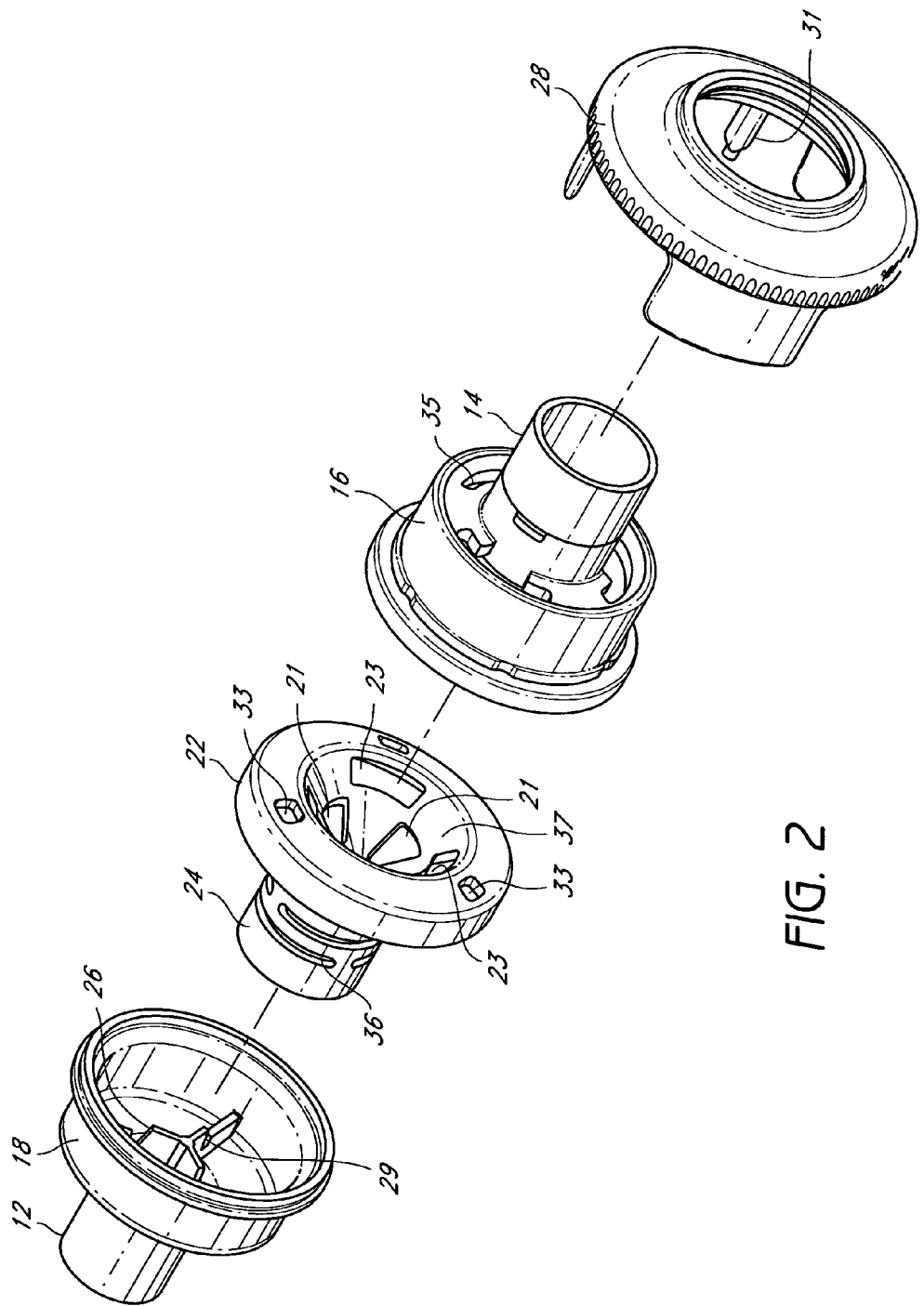
FIG. 2 is an exploded view of the device illustrating the major components in disassembled relationship.
Figure 7:
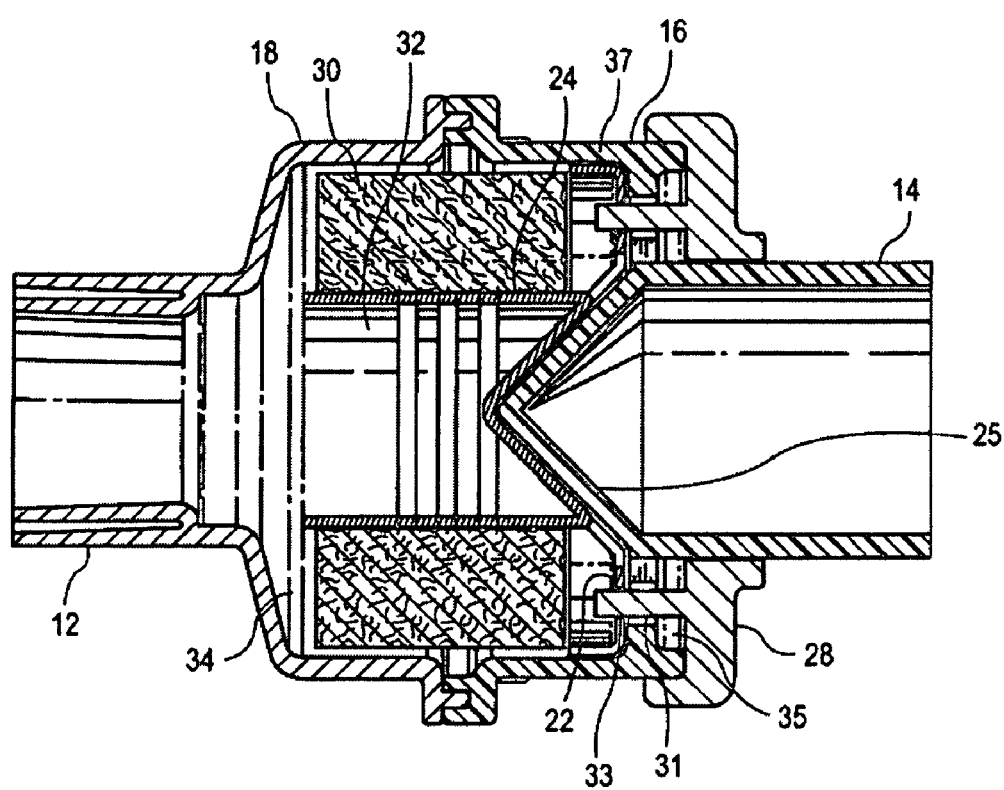
FIG. 7 is a sectional view of the assembled device.

Major components of the HME device assembly are illustrated in FIG. 2 showing the components disassembled but in relationship when assembled. The housing defining an interior chamber comprises a housing assembly having a first housing wall 16 and second housing wall 18 which are bonded or locked together or otherwise secured in a fixed or stationary position relative to one another. Conveniently the facing or mating edges of the housing members are secured as also shown in FIG. 7 with the mating edges glued or otherwise substantially permanently bonded with an adhesive or ultrasonically welded or the like. Alternatively, the housing components may be snap locked or in threaded engagement to provide access to interior components.

Figure 3:
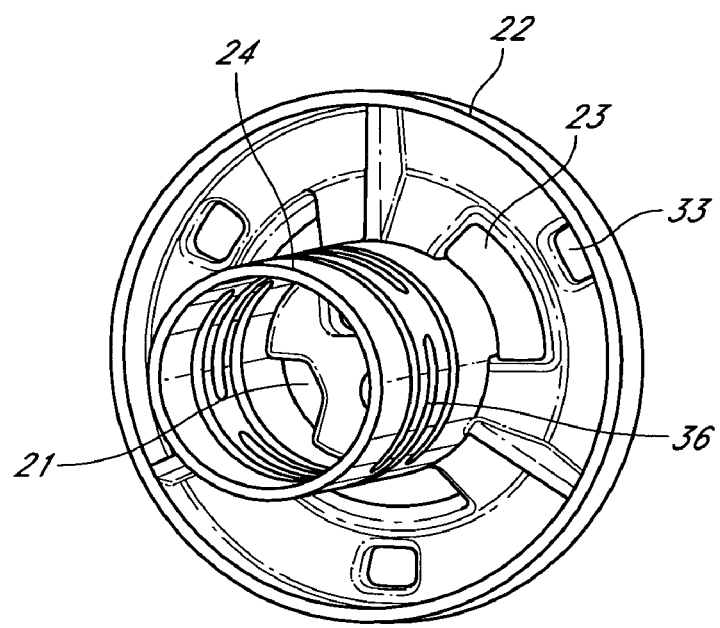
FIG. 3 is a perspective view of a rotatable apertured member.
Figure 4:
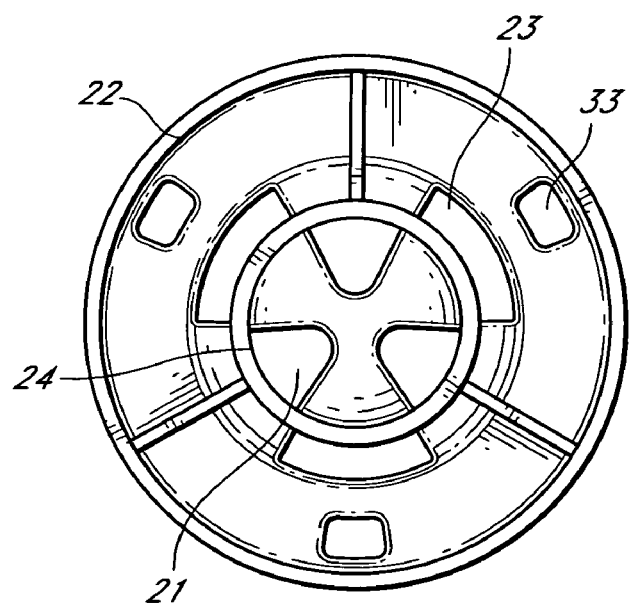
FIG. 4 is an end view of the member shown in FIG. 3.
Figure 5:
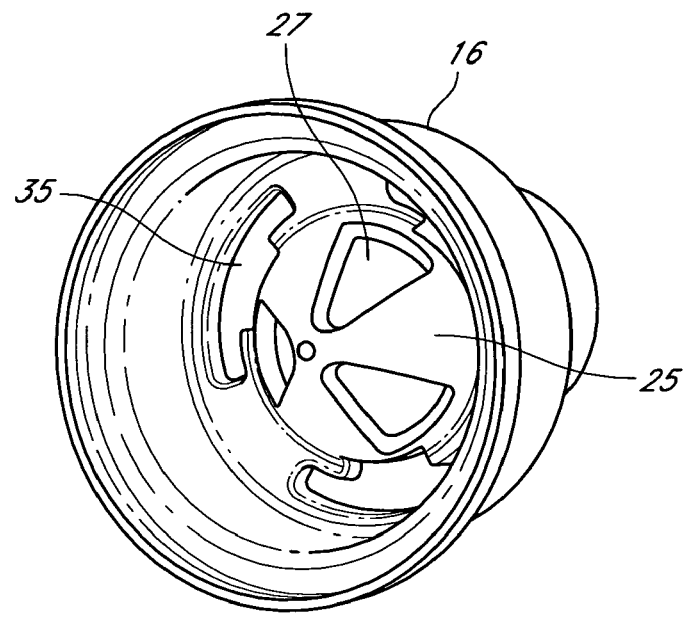
FIG. 5 is a perspective view of a housing member and attached stationary apertured member.
Figure 6:
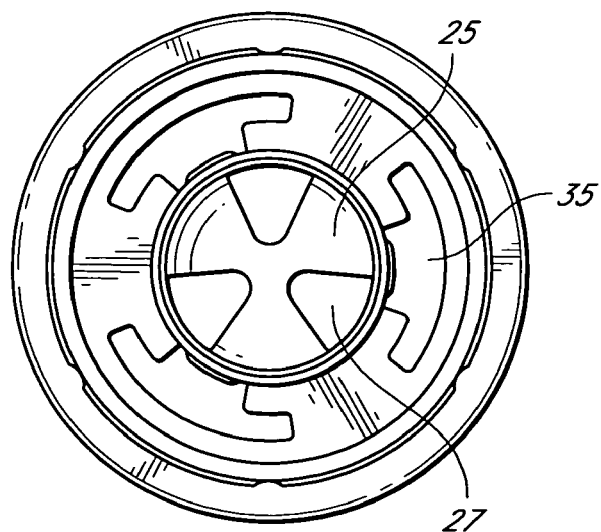
FIG. 6 is an end view of an assembly shown in FIG. 5.

Referring again to FIGS. 2-7, the valve for selectively directing fluid through the heat and moisture exchange device comprises two apertured members, one of which is fixed or stationary relative to the housing, and the other is movable, preferably rotatable, relative to the housing. Both of the apertured members comprise a plurality of apertures which are selectively aligned for directing a fluid through the device, between the opposite end pipes, in either HME mode or bypass mode. In the preferred embodiment illustrated in the drawings, apertured member 25 is formed as a unitary component with housing wall 16. The apertured member 25 comprises a wall having a plurality of fluid directing apertures 27 formed in the wall. In the preferred embodiment shown in FIGS. 2-4, a plurality of first apertures 21 and a plurality of second apertures 23 are formed on the rotational apertured member 22; a plurality of third apertures 27 are formed on stationary apertured member 25. Third apertures 27 are larger than apertures 21 or apertures 23. As apertured member 22 is rotated relative to apertured member 25, in a first valve position, first apertures 21 are aligned with apertures 27 of second apertured member 25 to provide a first fluid passage. In a second valve position, apertured member 22 is rotated so that the second apertures 23 are aligned with apertures 27 to provide a second fluid passage. In the valve position with apertures 21 and 27 aligned, apertures 23 are not aligned with any apertures in apertured member 25 whereby there is no passageway for gas flow through apertures 23. In a second valve position, with apertures 23 aligned with apertures 27, there is no alignment of apertures 21 with aperture 27 so that apertures 21 are closed to fluid flow. It is also to be understood that the apertured members as shown may be reversed, e.g., with the stationary member having first and second apertures and the rotatable member provided with third apertures. Moreover, the size and shape of the apertures shown, although preferred, are not limiting, and other relative sizes and shapes of apertures may be used to achieve the same performance.

The interior space or chamber defined by the housing walls between opposite pipes 12 and 14 is configured to provide a heat and moisture exchange passageway 34 and an elongated bypass passageway 32. As particularly illustrated in FIG. 7, bypass passageway 32 comprises an elongated generally circular conduit that is coaxial with pipes 12 and 14. The heat and moisture exchange passageway 34 is a generally annular space that is coaxial with the bypass passageway. As shown by arrows in FIG. 7, in one valve position, fluid flows through bypass passageway 32, and in another position through heat and moisture exchange passageway 34. Thus, fluid flow will be through one or the other of these two passageways, but not both, when the valve is positioned with rotatable apertured member 22 rotated so that either apertures 21 or 23 are further aligned with aperture 27 of apertured member 25. However, it will be understood that there will be intermediate positions where apertured member 22 is not fully rotated to the first or second valve positions whereby both of the apertures 21 and 23 will be partially aligned with apertures 27.

Positioned within the heat and moisture exchange passageway 34 is a heat and moisture exchange (HME) cartridge 30, as illustrated in the embodiment of FIG. 7. The HME cartridge is formed of a material and composition capable of absorbing moisture and heat from patient exhaled gas, and thereafter capable of releasing absorbed heat and moisture into dry respiratory gas flowing through the passageway. Such material is sometimes referred to as regenerative heat-moisture exchanger material. Examples of suitable material are disclosed in U.S. Pat. Nos. 5,042,468 and 5,592,933, the descriptions of which are incorporated herein by reference. Such material may be made of paper or other cellulosic material, for example, in the form of a honeycomb structure or helically wound strips of a corrugated mini-cardboard or cellulosic material to form an annular cartridge. Such material may be treated or impregnated with hygroscopic salts or compositions which will provide for good heat and moisture absorption and desorption. Other HME materials well known to those skilled in the art may also be used.

Prior to bonding the housing wall components together, the rotatable apertured member 22 is installed as is the HME material. As shown in FIG. 7, the rotatable apertured member 22 is assembled with apertured wall 37 of first apertured member 22 rotatably positioned adjacent to apertured wall 25. In the embodiment illustrated, pipe 14 at the opposite end of the housing from pipe 12 is unitary with first housing wall 16 and which housing is also provided with channels 35 through which components of valve selector 28 extend. Observing FIGS. 2 and 7, valve selector 28 is provided with valve selector pins 31 which extend through channels 35 and are inserted through slots 33 in rotatable apertured member 22. As so mounted, when valve selector 28 is rotated, the rotation is transferred to rotatable member 22 via the movement of the valve selector pins.

In the embodiment illustrated, a cylindrical tube or conduit is provided along at least a portion of the length of bypass passageway 32. The cylindrical tube provides a coaxial spool for supporting an annular cartridge or roll of the HME material which may be wrapped around the cylindrical conduit. In a preferred embodiment, the cylindrical tube is formed as an integral part of rotatable apertured member 22. The tube is preferably long enough so that the end opposite the valve is received in or otherwise supported by a spacer 26 formed as a component of housing wall member 18. A plurality of notches 29 are illustrated in FIG. 2 into which the end of the cylindrical tube 24 is rotatably received. In the preferred embodiment illustrated, tube 24 is also provided with slots 36 which allow a thermoplastic cylindrical material to be compressed because of the space of the slots whereby the cylinder acts as a biasing member for urging rotatable apertured member 22 against stationary apertured member 25 when the housing wall members 16 and 18 are sealed together in the fully assembled condition illustrated in FIGS. 1 and 7. The plurality of slots 36 may also be substituted with one or more spiral slots along the thermoplastic cylindrical material which will also create a yield or compressible feature to form the bias as described. Alternatively, a cylindrical tube need not be used, in which case it may be preferred to coat or seal the inner surface of the HME material exposed along the bypass passageway to reduce or prevent substantial aerosol absorption.

In operating the HME devices, when aerosol is to be delivered to a patient, the valve selector is rotated to a HME bypass or nebulizer position whereby the rotatable apertured member 22 is rotated to align apertures 21 with apertures 27 on apertured member 25 so that substantially all gas directed through the device bypasses the HME passageway. In the bypass mode, the HME device operates to direct the aerosol-gas mixture from pipe 14 through the elongated passageway 32 to pipe 12. When aerosol delivery to the patient is eliminated or terminated, the valve selector is rotated to align apertures 23 in apertured member 22 with apertures 27, and whereby apertures 21 are not in alignment. In this HME mode of operation, substantially all of the gas is delivered between pipes 12 and 14 through HME passageway 34. When the valve selector is rotated, there is no rotational movement of the housing wall structure or housing wall components 16 and 18 relative to one another nor rotational movement of pipes 12 and 14 relative to one another. Thus, the HME mode and bypass mode can be selected by an operator without transferring rotation to a patient circuit. The device may be operated by holding the housing with one hand and rotating the valve selector with the other hand without transferring rotational movement to either the patient, proximal pipe 12 side, or ventilator, distal pipe 14 side, so that the connections to the tubing on both sides of the device are not disturbed, loosened or otherwise disconnected.

What is claimed is:

1. A heat and moisture exchange device for respiratory therapy comprising:

a housing comprising a wall structure defining an interior chamber, said wall structure having a first pipe formed at one end thereof extending from a first housing wall and a second pipe formed at an opposite end thereof extending from a second housing wall, said pipes communicating with said interior chamber, and wherein mating edges of the first housing wall and the second housing wall are fixed directly to each other such that said wall structure housing walls and said first and second pipes are configured to be stationary relative to one another;

an elongated conduit along said interior chamber between said first and second pipes;

an absorbent material configured to alternatively absorb and desorb heat and moisture therefrom positioned in said interior chamber between said elongated conduit and said housing; and a valve having a valve selector operatively secured to said housing and a rotating apertured member enclosed entirely inside said housing to provide selective fluid communication in a first valve position through said conduit and bypassing said absorbent material and in a second valve position between said first and second pipe through said absorbent material, said valve providing said selective fluid communication without moving said first and second housing walls or said first and second pipes relative to one another; and wherein said valve comprises a first apertured member defining a plurality of first apertures and a plurality of second apertures therein and a second apertured member defining a plurality of third apertures therein, and wherein in said first valve position said valve provides fluid flow through said first and third apertures and in said second valve position said valve provides fluid flows through said second and third apertures.

2. A device of claim 1 wherein said first apertured member is the rotating apertured member and is movable relative to said housing and said second apertured member is a component wall of the housing stationary relative to said housing, and wherein said valve selector is configured to move said rotating first apertured member relative to said stationary second apertured member between said first and second valve positions.

3. A device of claim 2 wherein said valve selector is rotatably mounted on said housing in a configuration for rotating said rotating apertured member relative to said second apertured member without moving said housing or said first and second pipes relative to one another.

4. A heat and moisture exchange device for respiratory therapy comprising:

a walled housing having a first pipe secured at a first end thereof, and a second pipe secured at a second end thereof, opposite said first end, said housing defining chamber in fluid communication with said first and second pipes;

a regenerative heat-moisture exchanger material positioned in said chamber around a conduit inside the chamber to define a first fluid passageway between said first and second pipes through the conduit bypassing said heat-moisture exchanger material, and a second fluid passageway between said first and second pipes through said heat-moisture exchanger material;

a valve including
  a stationary apertured wall fixed in said walled housing, and
  a rotatable apertured member cooperating with said stationary apertured wall to selectively direct a fluid flow through said chamber along said first fluid passageway or said second fluid passageway, the heat-moisture exchanger material and rotatable apertured member both secured entirely inside the chamber of said walled housing; and a valve selector rotatably mounted on said walled housing to rotate said rotatable apertured member without moving said first and second pipes relative to one another, the valve selector rotating said rotatable apertured member between
  a first valve position to open fluid flow through the first fluid passageway and close fluid flow through the stationary apertured wall into said heat-moisture exchanger material, and
  a second valve position to open fluid flow through the second fluid passageway; and wherein the rotatable apertured member defines a first plurality of apertures and a second plurality of apertures, and the stationary apertured wall defines a third plurality of apertures; and in the first valve position the first plurality of apertures are aligned only with the third plurality of apertures to open fluid flow through the first fluid passageway and close fluid flow through the third plurality of apertures into said heat-moisture exchanger material, and in the second valve position the second plurality of apertures are aligned only with the third plurality of apertures to open fluid flow through the second fluid passageway and close fluid flow through the conduit.

5. The device of claim 4, wherein said conduit comprises a cylindrical tube.

6. The device of claim 5, wherein said cylindrical tube is an integral part of the rotatable apertured member and includes one or more slots, and the tube acts as a biasing member for urging the rotatable apertured member against the stationary apertured wall.

7. The device of claim 4,
wherein the valve selector includes one or more selector pins extending through channels defined by said walled housing and inserted into one or more corresponding slots defined by said rotatable apertured member.

8. The device of claim 4, wherein the stationary apertured wall is conical.

9. A heat and moisture exchange device for respiratory therapy comprising:

a walled housing having a first pipe secured at a first end thereof, and a second pipe secured at a second end thereof, opposite said first end, said housing defining chamber in fluid communication with said first and second pipes;

a regenerative heat-moisture exchanger material positioned in said chamber around a conduit inside the chamber to define a first fluid passageway between said first and second pipes through the conduit bypassing said heat-moisture exchanger material, and a second fluid passageway between said first and second pipes through said heat-moisture exchanger material;

a valve including
  a stationary apertured wall fixed in said walled housing, and
  a rotatable apertured member cooperating with said stationary apertured wall to selectively direct a fluid flow through said chamber along said first fluid passageway or said second fluid passageway, the heat-moisture exchanger material and rotatable apertured member both secured entirely inside the chamber of said walled housing; and a valve selector rotatably mounted on said walled housing to rotate said rotatable apertured member without moving said first and second pipes relative to one another, the valve selector rotating said rotatable apertured member between
  a first valve position to open fluid flow through the first fluid passageway and close fluid flow through the stationary apertured wall into said heat-moisture exchanger material, and a second valve position to open fluid flow through the second fluid passageway; and wherein the rotatable apertured member defines a first plurality of apertures, and the stationary apertured wall defines a second plurality of apertures and a third plurality of apertures; and in the first valve position the first plurality of apertures are aligned only with the second plurality of apertures to open fluid flow through the first fluid passageway and close fluid flow through the third plurality of apertures into said heat-moisture exchanger material, and in the second valve position the first plurality of apertures are aligned only with the third plurality of apertures to open fluid flow through the second fluid passageway and close fluid flow through the conduit.

10. The device of claim 9, wherein said conduit comprises a cylindrical tube.

11. The device of claim 10, wherein said cylindrical tube is an integral part of the rotatable apertured member and includes one or more slots, and the tube acts as a biasing member for urging the rotatable apertured member against the stationary apertured wall.

12. The device of claim 9,
wherein the valve selector includes one or more selector pins extending through channels defined by said walled housing and inserted into one or more corresponding slots defined by said rotatable apertured member.

13. The device of claim 9, wherein the stationary apertured wall is conical.

* * * * *